(12) United States Patent
Ferhanoglu et al.

(10) Patent No.: US 12,708,275 B2
(45) Date of Patent: Aug. 18, 2026

(54) MAGNETIC RESONANCE (MR) COMPATIBLE OVER-FIBER MULTI-SENSOR SYSTEM

(71) Applicants: ISTANBUL TEKNIK UNIVERSITESI, Istanbul (TR); BOGAZICI UNIVERSITESI DONER SERMAYE ISLETME MUDURLUGU, Istanbul (TR); TURK-ALMAN UNIVERSITESI, Istanbul (TR)

(72) Inventors: Onur Ferhanoglu, Istanbul (TR); Parviz Zolfaghari, Istanbul (TR); Arda Deniz Yalcinkaya, Istanbul (TR); Oguz Kaan Erden, Istanbul (TR); Murat Tumer, Istanbul (TR)

(73) Assignees: ISTANBUL TEKNIK UNIVERSITESI, Istanbul (TR); BOGAZICI UNIVERSITESI DONER SERMAYE ISLETME MUDURLUGU, Istanbul (TR); TURK-ALMAN UNIVERSITESI, Istanbul (TR)

( * ) Notice: Subject to any disclaimer, the term of this patent is extended or adjusted under 35 U.S.C. 154(b) by 235 days.

(21) Appl. No.: 18/725,883

(22) PCT Filed: Dec. 27, 2022

(86) PCT No.: PCT/TR2022/051634
§ 371 (c)(1),
(2) Date: Jul. 1, 2024

(87) PCT Pub. No.: WO2023/129064
PCT Pub. Date: Jul. 6, 2023

(65) Prior Publication Data

US 2025/0120596 A1 Apr. 17, 2025

(30) Foreign Application Priority Data

Dec. 29, 2021 (TR) ............................... 2021/021642

(51) Int. Cl.
*A61B 5/00* (2006.01)
*A61B 5/0205* (2006.01)
(Continued)

(52) U.S. Cl.
CPC ...... *A61B 5/02055* (2013.01); *A61B 5/02154* (2013.01); *A61B 5/062* (2013.01);
(Continued)

(58) Field of Classification Search
CPC . A61B 5/02055; A61B 5/02154; A61B 5/062; A61B 5/055; A61B 2562/0233;
(Continued)

(56) References Cited

U.S. PATENT DOCUMENTS 9,554,738 B1 * 1/2017 Gulati .................. A61B 5/0075
10,376,160 B2 * 8/2019 Ishizawa ............ A61B 5/02108
(Continued)

FOREIGN PATENT DOCUMENTS

DE 102021206761 A1 * 12/2022 ........... A61B 5/0077
EP 3139833 B1 * 7/2022 ........ A61M 16/0003
(Continued)

OTHER PUBLICATIONS

Optical fiber-based MR-compatible sensors for medical applications: an overview (Year: 2013).*

*Primary Examiner* — May A Abouelela
(74) *Attorney, Agent, or Firm* — Bayramoglu Law Offices LLC

(57) ABSTRACT

A multi-sensor system is provided and integrated on one or more fibers, compatible with magnetic resonance (MR) imaging, capable of measuring temperature, pressure, and
(Continued)

position during medical interventional procedures (ablation, catheter insertion into the body, etc.). The multi-sensor system includes a perforated membrane structure, a pressure measuring membrane, a semiconductor die, and a magnetic material.

8 Claims, 5 Drawing Sheets

(51) Int. Cl.
*A61B 5/0215* (2006.01)
*A61B 5/06* (2006.01)
*G01R 33/28* (2006.01)
*A61B 5/055* (2006.01)

(52) U.S. Cl.
CPC ............ *G01R 33/286* (2013.01); *A61B 5/055* (2013.01); *A61B 2562/0233* (2013.01)

(58) Field of Classification Search
CPC ..... A61B 5/02152; A61B 5/0075; A61B 5/01; A61B 2562/0247; A61B 2562/0271; A61B 2562/18; G01R 33/286; G01R 33/28
See application file for complete search history.

(56) References Cited

U.S. PATENT DOCUMENTS 12,161,445 B2 * 12/2024 Siedenburg .......... A61B 5/6833
2005/0001615 A1 * 1/2005 Sato ...................... A61B 5/055 324/306
2009/0093728 A1 * 4/2009 Hyde ..................... A61B 5/061 606/41
2013/0338512 A1 * 12/2013 Warren .............. A61B 5/14552 600/479
2015/0377997 A1 * 12/2015 Zabow ............... G01R 33/5601 324/309
2017/0143234 A1 * 5/2017 Degertekin ............ A61B 5/061
2018/0064481 A1 * 3/2018 Coulombe ............... A61B 5/01
2020/0357098 A1 * 11/2020 Yoo ...................... A61B 6/5258
2020/0379071 A1 * 12/2020 Gong ................. G01R 33/5608
2021/0088605 A1 * 3/2021 Shi ......................... G01R 33/24
2021/0153766 A1 * 5/2021 Greiser ................ G01R 33/543
2021/0208219 A1 * 7/2021 Vester .................... G01R 33/28
2021/0386347 A1 * 12/2021 Moriya .................. A61B 5/245
2021/0386478 A1 * 12/2021 Capote ............... G01R 33/4804
2021/0389400 A1 * 12/2021 Oida ...................... G01R 33/26
2022/0013199 A1 * 1/2022 Kozloski ................ G16H 50/50
2022/0091206 A1 * 3/2022 Eberler .............. G01R 33/3804
2022/0257138 A1 * 8/2022 Gleich ................... A61B 5/062
2023/0309842 A1 * 10/2023 Alexander ......... A61B 5/02141 604/96.01
2024/0252060 A1 * 8/2024 Getman ................. A61B 5/746

FOREIGN PATENT DOCUMENTS

EP 4029440 A1 * 7/2022 ........... A61B 5/0205
EP 4035588 A1 * 8/2022 ........... A61B 5/0245
EP 3870043 B1 * 7/2023 ............. A61B 5/055
WO WO-2013182953 A1 * 12/2013 ............. A61B 34/20
WO WO-2020092747 A1 * 5/2020 ........... A61B 5/0024
WO WO-2023166525 A1 * 9/2023 ........... A61B 5/4815

* cited by examiner

MAGNETIC RESONANCE (MR) COMPATIBLE OVER-FIBER MULTI-SENSOR SYSTEM

CROSS-REFERENCE TO THE RELATED APPLICATIONS

This application is the national phase entry of International Application No. PCT/TR2022/051634, filed on Dec. 27, 2022, which is based upon and claims priority to Turkish Patent Application No. 2021/021642, filed on Dec. 29, 2021, the entire contents of which are incorporated herein by reference.

TECHNICAL FIELD

The invention relates to a multi-sensor system integrated on one or more fibers, compatible with magnetic resonance (MR) imaging, capable of measuring temperature, pressure, and position during medical interventional procedures (ablation, catheter insertion into the body, etc.).

BACKGROUND

A magnetic resonance (MR) compatible pressure or magnetic resonance (MR) compatible temperature sensor is available separately.

Furthermore, radio-frequency (RF) based antenna structures are frequently used for position detection within the MR imaging unit but they also have the possibility of heating inside the body.

In the publication document titled MRI Compatible Fiber Optic Multi-Sensor Platform for Real-Time Vital Monitoring, a fiber optic-based multi-sensor platform compatible with magnetic resonance imaging (MRI) that enables real-time monitoring of vitals is disclosed.

In the publication document titled Optical Fiber-Based MR-Compatible Sensors for Medical Applications: An Overview, magnetic resonance-compatible optical fiber-based sensors used in medical applications are disclosed. It is described that these sensors are used to measure temperature, pressure, force, position, etc.

The Japanese patent document numbered JP2018536859A discloses a pressure sensor or a sensor system comprising one or more pressure sensors.

When the systems in the art are examined, the existing systems consist of a probe and catheter-type devices that can only measure temperature, only pressure, or only position (under MR).

In this context, there is a need to develop a multi-sensor system that can measure temperature, pressure, and position simultaneously for medical or industrial applications (where magnetic fields are present), which is not available in existing systems.

SUMMARY

The object of the present invention is to realize a multi-sensor system compatible with magnetic resonance (MR) imaging, capable of measuring temperature, pressure, and position during medical interventional procedures (ablation, catheter insertion into the body, etc.).

Another object of the present invention is to realize a multi-sensor system that is compatible with magnetic resonance (MR) imaging and does not cause heating inside the body while measuring temperature, pressure, and position during medical interventional procedures (ablation, catheter insertion into the body, etc.).

BRIEF DESCRIPTION OF THE DRAWINGS

The magnetic resonance-compatible multi-sensor system realized to achieve the objects of the present invention is shown in the attached figures.

These figures are as follows.

The parts in the figures are individually numbered and the corresponding numbers are given below.

Figure 1:
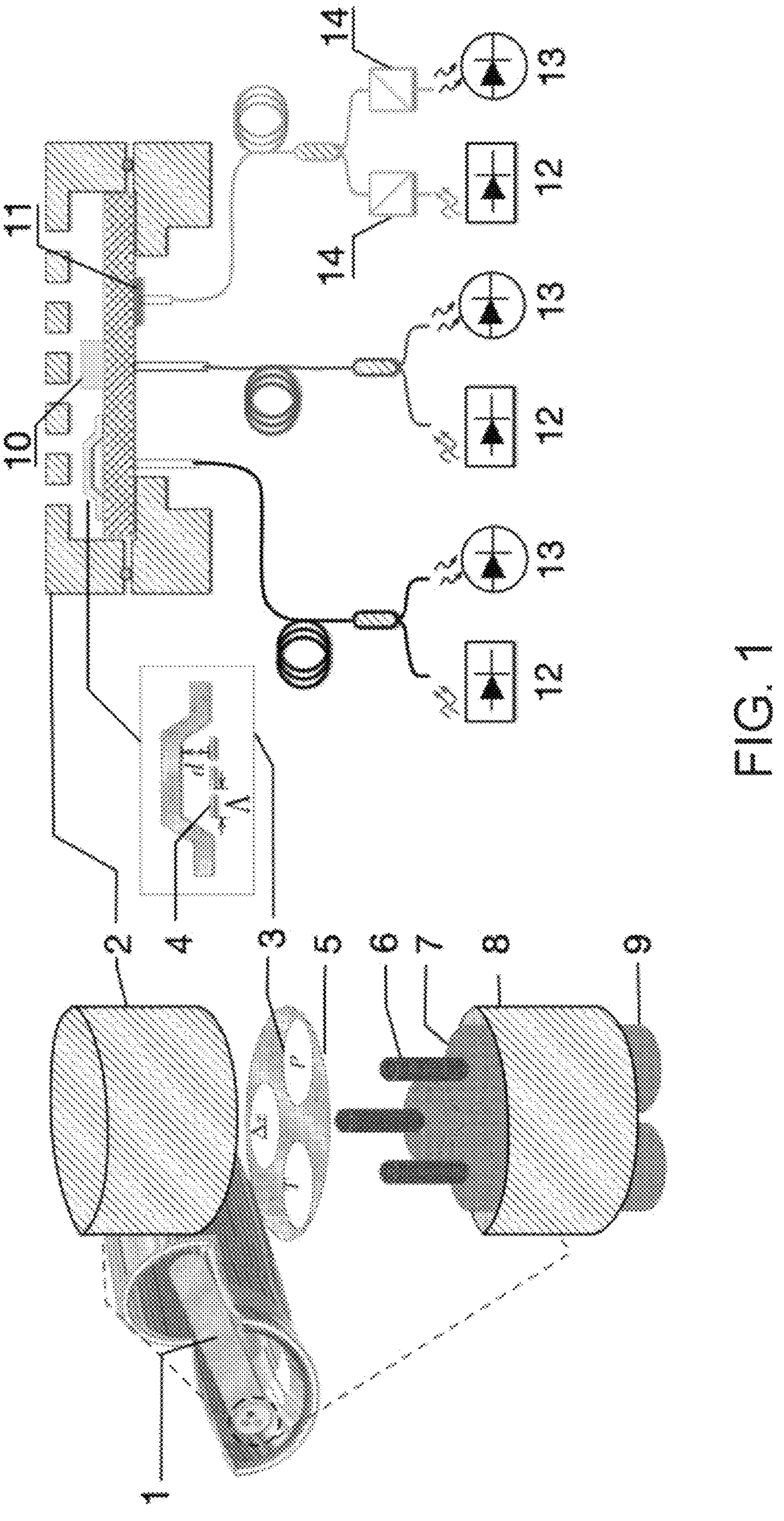
FIG. 1: A schematic view of the multi-sensor system of the invention.
Figure 2:
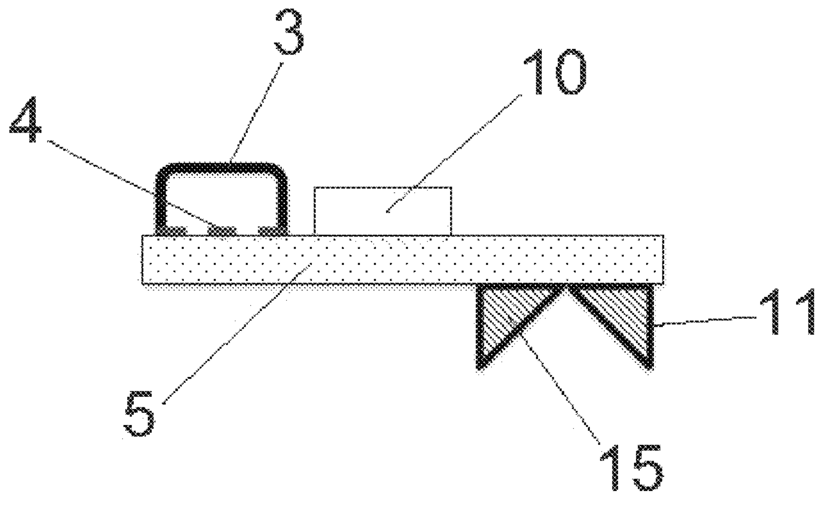
FIG. 2: A view of the system of the invention in a different embodiment in which the sensors are discrete (side by side).
Figure 3:
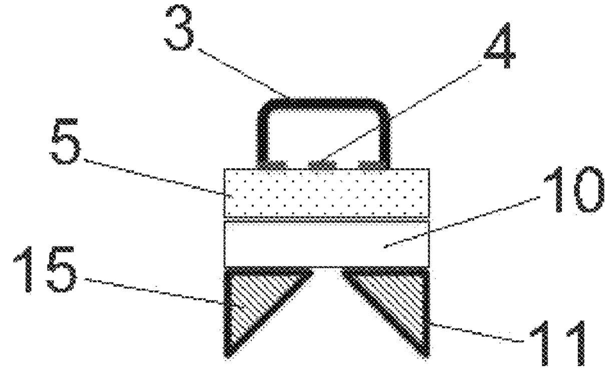
FIG. 3: A view of the system of the invention in a different embodiment in which the sensors are integrated (on top of each other).
Figure 4:
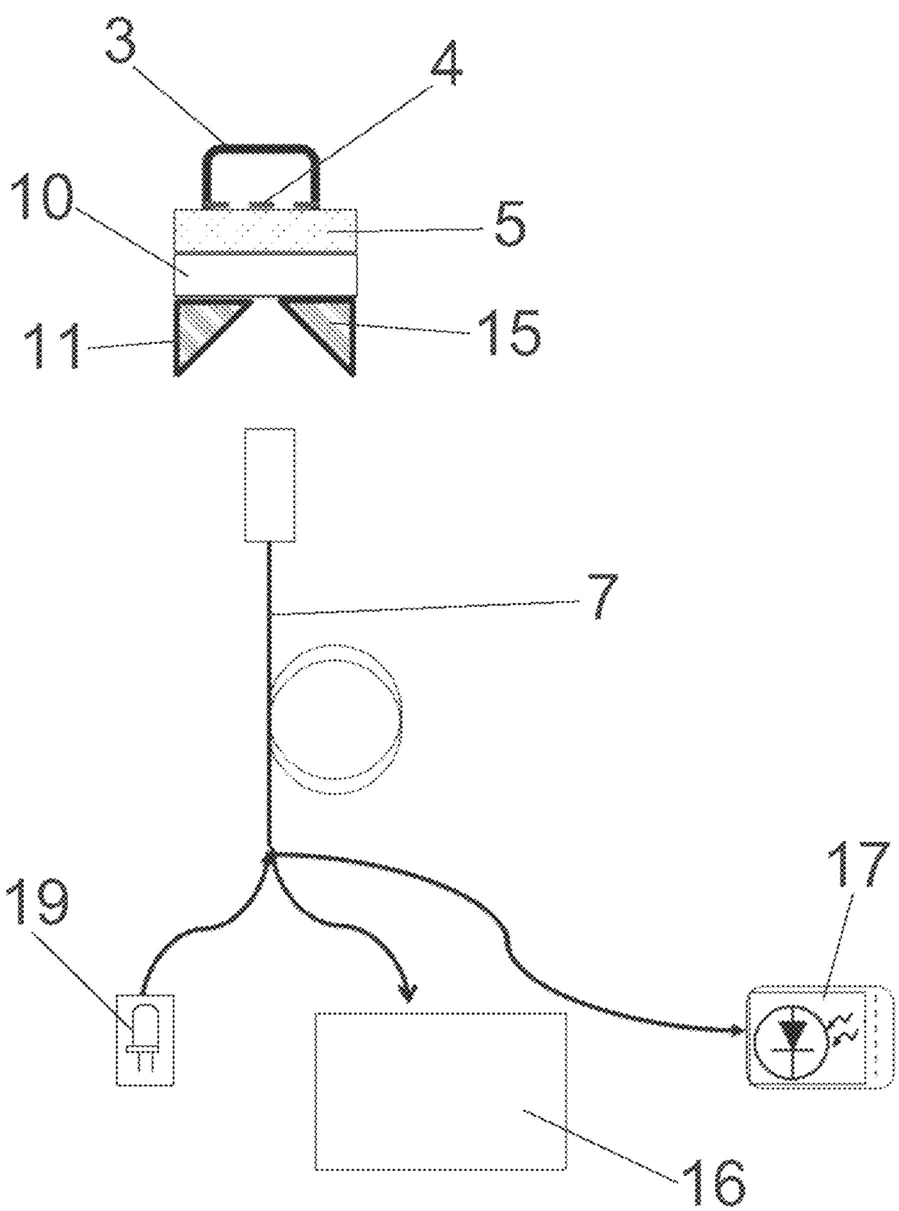
FIG. 4: A schematic view of data acquisition from the multi-sensor system of the invention.
Figure 5:
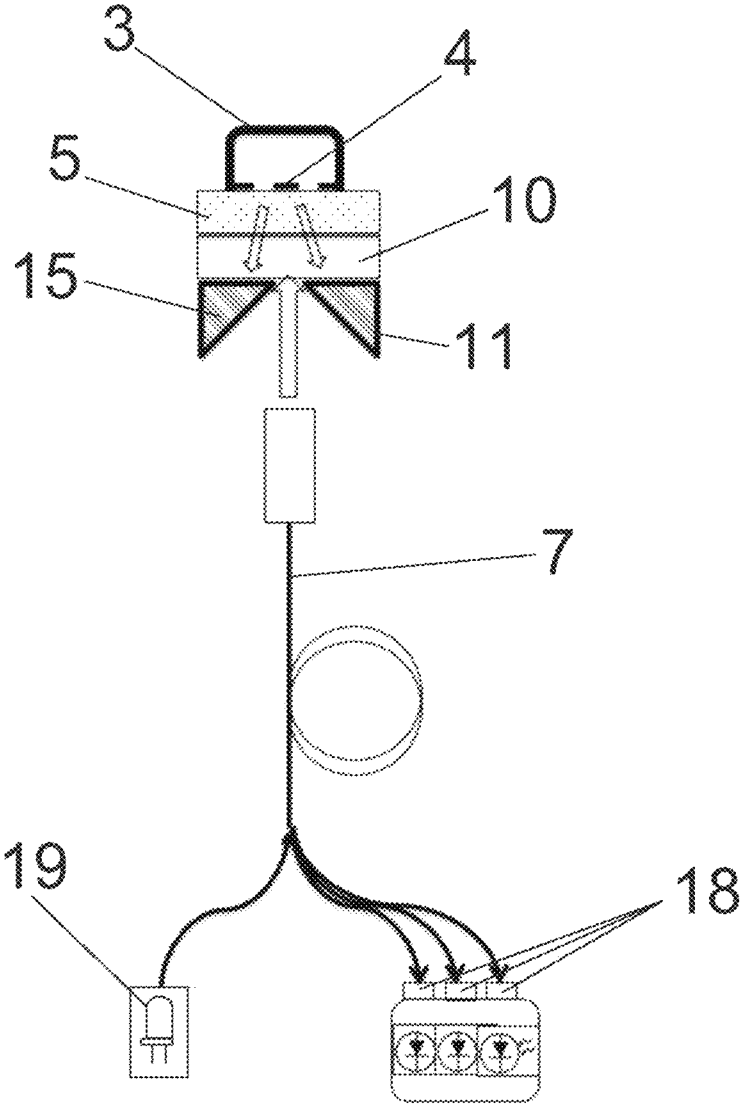
FIG. 5: A schematic view of the data acquisition from the multi-sensor system of the invention in a different case.

1. Multi-sensor system
2. Perforated membrane structure
3. Pressure measuring membrane
4. Diffraction grating
5. Substrate
6. Laser beam
7. Fiber optic cable
8. Fiber adapter
9. Fiber sheath
10. Semiconductor die
11. Magnetic material
12. Light source
13. Photo-sensor
14. Polarizer
15. Prism
16. Spectrometer
17. Polarimeter
18. Optical filter
19. Broadband light source
A. Semiconductor transition wavelength
B. Semiconductor transition wavelength range
C. Position measurement wavelength range
D. Pressure measurement wavelength range

DETAILED DESCRIPTION OF THE EMBODIMENTS

The magnetic resonance (MR) compatible multi-sensor system (1) of the invention comprises the following parts;

- a perforated membrane structure (2) in the form of a perforated cap located at the distal end of the multi-sensor system (1), which enables the blood in the vessel to contact with the system,
- a pressure measuring membrane (3) consisting of one or more layers of material, which is used for measuring the pressure of blood or ambient fluid, planarly positioned on a substrate (5), and a diffraction grating (4) planarly positioned thereunder to create interference on incident light,
- a fiber optic cable (7) which carries a laser beam (6) directed onto the substrate (5) and is used for collecting the light returned from the sensors,

- a semiconductor die (10) placed planarly on the bottom of the substrate (5), within the perforated membrane structure (2) that measures temperature the temperature dependence of the energy-bandgap of a semiconductor crystal,
- a magnetic material (11), which is located in the perforated membrane structure (2) and placed on the bottom surface of the substrate (5) on planar or prism (15) structures with different plane angles, based on the observation of the polarization change of light reflected therefrom as a position sensor in environments where the magnetic field changes with respect to position, such as magnetic resonance (MR) imaging.
- light sources (12) for taking measurements from each sensor,
- photo-sensors (13) for measuring the amount of light returned from the sensor,
- two linear polarizers (14) for observing the polarization change of light returned from the magnetic material (11),
- prisms (15) for increasing the sensitivity of the Magnet-optical Kerr effect,
- a spectrometer (16) for providing sensor data (pressure and temperature) by simultaneously sensing different wavelengths,
- a polarimeter (17) for reading the position information and capable of measuring the angle and linearity of polarization,
- optical filters (18) for filtering the wavelengths at which different sensors are to be read as an alternative to a spectrometer (16) based optical reading.

The pressure measuring membrane (3) and diffraction grating (4) are used to measure pressure. The pressure measuring membrane (3) and the diffraction grating (4) form two different surfaces of an interferometer. One part of the light passing through the substrate (5) hits the diffraction grating (4) and the other part hits the pressure measuring membrane (3) so that the movement of the membrane (3) against the pressure can be measured.

The substrate (5) can be transparent to visible light substrates such as die, Quartz/Pyrex on which the sensors are produced and/or integrated with micro-fabrication techniques, or different material options can be used.

The laser beam (6) is used to measure the parameters (pressure, temperature, position) measured by the sensors. It is transmitted to the sensors through a fiber optic cable (7). A miniature lens (GRIN type, aspherical or spherical) can be used in front of the fiber to prevent the laser from scattering at different angles.

The fiber adapter (8) is in the form of a flexible reservoir and houses the fibers in the fiber optic cable (7).

The fiber sheath (9) wraps the fiber optic cable (7) and protects the fiber optic cable (7) against possible damage.

The semiconductor die (10) is used to measure temperature. Typical semiconductors such as Silicon or Gallium Arsenide and/or combinations of materials between columns III-V of the periodic table can be used.

The magnetic material (11) can be used as a position sensor in environments where the magnetic field is present and changes with respect to position, such as MR imaging.

The light source (12) consists of one or more lasers, LEDs, and/or SLEDs (superluminescent diodes) leading to the sensors.

The polarizer (14) is used to observe the polarization change of the light returned from the magnetic material (11). In the system subject to the invention, there are two linear polarizers (14) for polarizing the light going to the sensor and measuring the transmittance of the light returning from the sensor at a certain polarization.

The prism (15) is involved in increasing the sensitivity of the Magnet-optical Kerr effect. Light strikes the magnetic material (11) at the hypotenuse angle of the prism (15). The use of two prisms (15) also ensures that the light returns to the fiber from which it came after hitting the magnetic material (11).

Figure 6:
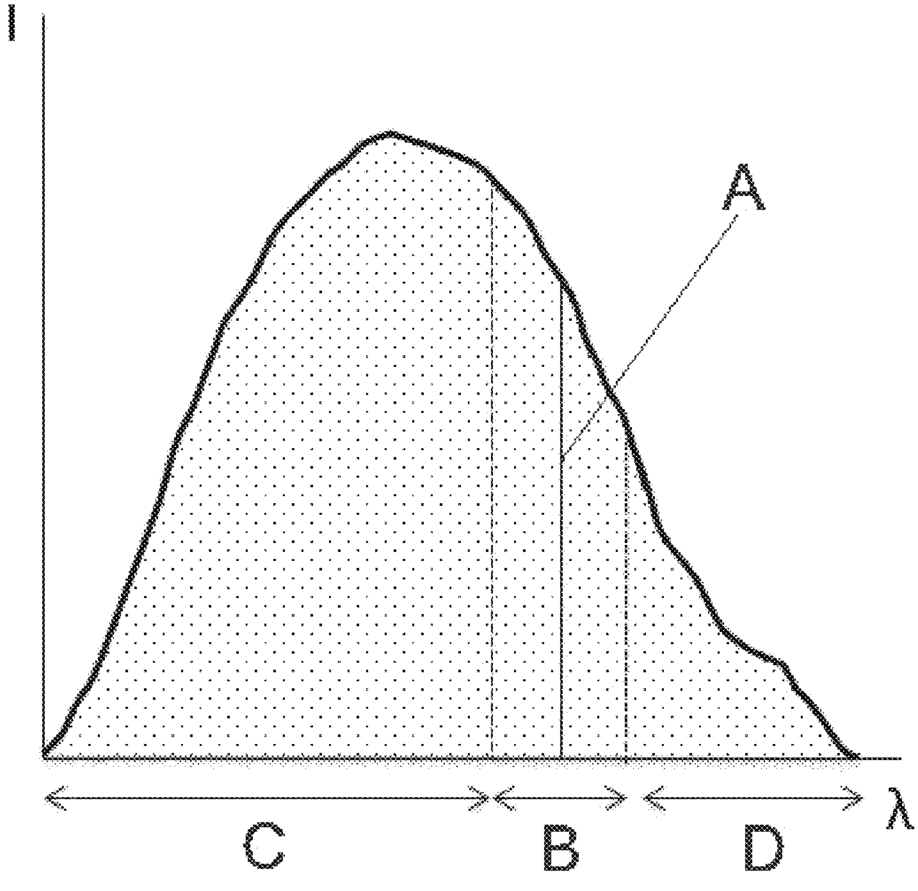
FIG. 6: A graphical representation of the spectral range used in the multi-sensor system of the invention.

In the graph in FIG. 6, the semiconductor transition wavelength (A) is the wavelength corresponding to the forbidden energy-bandgap of the semiconductor temperature meter at nominal (room) temperature. Beyond this wavelength (at larger wavelengths) the material is transparent, whereas beyond it (at smaller wavelengths) it is absorptive.

The range of values (B) that the semiconductor transition wavelength can take in the temperature range targeted to be measured with the semiconductor is also shown in FIG. 6.

The position measurement wavelength range (C) is the wavelength range corresponding to the part of the light reflected from the sensors and will be used for position measurement. In this wavelength range, the part of the light corresponding to the semiconductor material will be absorbed, but the polarization change of the part of the light hitting the prisms (15) covered with magnetic material (11) will be observed by means of a polarizer (14) to obtain position information.

The pressure measurement wavelength range (D) is the wavelength range corresponding to the portion of the light that can pass through the sensors and will be used for pressure measurement. After passing through the stack of sensors, the light reflects off the reflective layers of the pressure sensor (diffraction grating (4) and membrane (3)) and returns the way it came. Light can pass through the semiconductor material in this wavelength range. When more than one wavelength is used in this range, the range of displacement (and therefore pressure) that the interferometer can measure increases.

The optical filter (18) is used to filter the wavelengths at which different sensors will be read as an alternative to a spectrometer (16) based optical reading. In this case, as many photodetector units as the number of filters can be used instead of the spectrometer (16). (Minimum 3 filter and photodetector pairs are required for three sensors).

In the system of the invention, temperature sensing is realized by utilizing the principle that the amount of absorption of light (related to the bandgap) sent to the semiconductor die ( ) (Silicon, Galium Arsenide, or other semiconductors) changes according to the temperature.

Pressure sensing operation comprises the bending response of a miniaturized membrane (3) structure consisting of one or more layers to pressure and the measurement of this bending response using an interferometric principle. The thickness of the layers on the membrane (3) structure can be adjusted to ensure that the membrane (3) does not bend (temperature insensitivity is eliminated) against temperature.

Position measurement is performed using the magneto-optic Kerr effect (MOKE), which is based on the polarization change of light incident on a magnetic film with respect to a magnetic field. To make the most of the MOKE effect, the magnetic film is placed at an angle of 30 to 60 degrees to the optical plane. In this context, the magnetic film is coated on one or more miniature prism (15) structures.

All three sensor structures placed in the system subject to the invention can be produced and/or integrated into the same plane on a substrate (5). In this case, external laser and/or light sources (12) are coupled to three fiber optic cables (7). With a miniature lens placed at the end of the fiber optic cable (7), the expansion of the light is prevented and collimated, and each light source (12) is directed to the respective sensor. The light data returned from the sources can be collected by fiber optic cables (7). The returned light can be sent to three external photo-sensor units (13) for parameter (temperature, position, and pressure) estimation.

Alternatively, all three sensors can be used in a stacked array; the semiconductor-based temperature measurement device can be integrated under the pressure measuring membrane (3) structure, while the magnetic material (11), where the MOKE effect (position sensing) will be observed, can be integrated under the semiconductor temperature gauge.

In this case, a single fiber optic cable (7) can be used to carry light to all three sensors.

A broadband light source (19) should be coupled to a fiber optic cable (7). Different wavelengths of the light spectrum will be used to carry data to different sensors and to detect the signal of interest. The lowest wavelength of the light source (12) band shall be used for position detection, the median wavelengths for temperature measurement, and the highest band of the light source (12) for pressure measurement.

In order to be able to observe different wavelengths in the analysis of the data, a spectrometer (16) is required instead of the photodetector units.

For MR imaging or position determination in the presence of a magnetic field, the polarization of light must be observed. For this purpose, a polarizer (14) can be placed in front of the spectrometer (16) or polarization information can be obtained by directing low wavelengths to a polarimeter (17) instead of the spectrometer (16).

What is claimed is:

1. A magnetic resonance (MR) compatible multi-sensor system, comprising the following parts; a perforated membrane structure in a form of a perforated cap located at a distal end of the MR compatible multi-sensor system, wherein the perforated membrane structure configure blood in a vessel to contact with the MR compatible multi-sensor system, a pressure measuring membrane consisting of at least one layer of material, wherein the pressure measuring membrane is configured for measuring a pressure of blood or ambient fluid, planarly positioned on a substrate, and a diffraction grating planarly positioned thereunder to create an interference on an incident light, a semiconductor die placed planarly on a bottom of the substrate, within the perforated membrane structure, wherein the semiconductor die measures a temperature and a temperature dependence of an energy-bandgap of a semiconductor crystal, a magnetic material, wherein the magnetic material is located in the perforated membrane structure and placed on a bottom surface of the substrate on planar or prism structures with different plane angles, based on an observation of a polarization change of light reflected therefrom as a position sensor in environments where a magnetic field changes with respect to position, comprising MR imaging.

2. The MR compatible multi-sensor system according to claim 1, wherein the MR compatible multi-sensor system comprises a fiber optic cable, wherein the fiber optic cable carries a laser beam directed onto the substrate and is for collecting the light returned from the multi-sensors.

3. The MR compatible multi-sensor system according to claim 1, wherein the MR compatible multi-sensor system comprises light sources for taking measurements from each sensor of the multi-sensor.

4. The MR compatible multi-sensor system according to claim 1, wherein the MR compatible multi-sensor system comprises photo-sensors for measuring an amount of light returned from the multi-sensor.

5. The MR compatible multi-sensor system according to claim 1, wherein the MR compatible multi-sensor system comprises two linear polarizers for observing the polarization change of light returned from the magnetic material.

6. The MR compatible multi-sensor system according to claim 1, wherein the MR compatible multi-sensor system comprises a spectrometer for providing sensor data by simultaneously sensing different wavelengths, wherein the sensor data comprises pressure and temperature.

7. The MR compatible multi-sensor system according to claim 1, wherein the MR compatible multi-sensor system comprises a polarimeter for reading position information and is allowed for measuring an angle and linearity of polarization.

8. The MR compatible multi-sensor system according to claim 1, wherein the MR compatible multi-sensor system comprises optical filters for filtering wavelengths where different sensors are to be read as an alternative to a spectrometer based optical reading.

* * * * *